United States Patent [19]

Westfechtel et al.

[11] Patent Number: 5,387,374

[45] Date of Patent: Feb. 7, 1995

[54] GUERBET CARBONATES

[75] Inventors: Alfred Westfechtel, Hilden; Frank Bongardt, Duesseldorf; Achim Ansmann, Erkrath, all of Germany

[73] Assignee: Henkel Kommanditgesellschaft auf Aktien, Duesseldorf, Germany

[21] Appl. No.: 78,211

[22] Filed: Jun. 15, 1993

[30] Foreign Application Priority Data

Dec. 15, 1990 [DE] Germany ............... 4040154

[51] Int. Cl.$^6$ ................ C10M 105/48; C07C 69/96
[52] U.S. Cl. ................ 252/56 S; 558/277
[58] Field of Search ........ 252/56 S; 558/277

[56] References Cited

U.S. PATENT DOCUMENTS

| | | | |
|---|---|---|---|
| 2,758,975 | 8/1956 | Cottle et al. | 252/49.8 |
| 4,395,370 | 7/1983 | Boden et al. | 260/463 |
| 4,447,365 | 5/1984 | Boden et al. | 260/463 |
| 4,522,765 | 6/1985 | Wiegers et al. | 260/463 |
| 4,604,242 | 8/1986 | Harley et al. | 558/260 |
| 5,009,803 | 4/1991 | Branddese | 252/49.5 |

FOREIGN PATENT DOCUMENTS

| | | |
|---|---|---|
| 0437764 | 12/1990 | European Pat. Off. |
| 2335728 | 1/1974 | Germany |
| 55-064550 | 5/1980 | Japan |
| 1129229 | 10/1968 | United Kingdom |

OTHER PUBLICATIONS

Fat. Sci. Technol. 89, 237 (1987).
Soap Cosm. Chem. Spec., 52 (1987).
J. Chem. Soc., 117, 708 (1920).
Houben–Weyl, Methoden der Organischen Chemie, 4th Ed., vol. E4, pp. 66 et seq. (1964).
DIN 51 601 (Feb. 1986).
DIN ISO 3015 (Oct. 1982).

*Primary Examiner*—Mary C. Lee
*Assistant Examiner*—Michael G. Ambrose
*Attorney, Agent, or Firm*—Ernest G. Szoke; Wayne C. Jaeschke; Henry E. Millson, Jr.

[57] ABSTRACT

Guerbet carbonates corresponding to formula (I)

$$R^1-O-\overset{\overset{\displaystyle O}{\|}}{C}-O-R^2 \qquad (I)$$

in which $R^1$ is a branched alkyl radical containing 12 to 44 carbon atoms and $R^2$ has the same meaning as $R^1$ or is a linear alkyl radical containing 1 to 12 carbon atoms; their use as lubricants; and a process for their preparation in which Guerbet alcohols are used to transesterify dialkyl carbonates of formula III $$R^3-O-\overset{\overset{\displaystyle O}{\|}}{C}-O-R^3 \qquad (III)$$

in which $R^3$ is a linear alkyl radical containing 1 to 12 carbon atoms.

6 Claims, No Drawings

GUERBET CARBONATES

This invention relates to Guerbet carbonates, to a process for their production and to their use as lubricants.

By virtue of their high molecular weight, esters of saturated fatty acids with long-chain saturated alcohols have excellent metal wetting and lubricating properties. On account of their high pour points, however, the products cannot be used for low-temperature applications (Fat. Sci. Technol. 89, 237 (1987)).

Wax esters having improved temperature behavior are obtained from unsaturated fatty acids and/or unsaturated fatty alcohols. Although such products as oleyl oleate or oleyl erucate, for example, are liquid at low temperatures, the double bonds present in the molecule make them vulnerable to oxidative damage which, in the most favorable case, can lead to unwanted discoloration and, in the worst case, to decomposition of the product.

Accordingly, the problem addressed by the present invention was to develop new lubricants which would be free from the disadvantages mentioned above.

The present invention relates to Guerbet carbonates corresponding to formula (I)

in which $R^1$ is a branched alkyl radical containing 12 to 44 carbon atoms and $R^2$ has the same meaning as $R^1$ or is a linear alkyl radical containing 1 to 12 carbon atoms.

It has surprisingly been found that the Guerbet carbonates according to the invention not only have good lubricating properties, they are also present as clear colorless liquids even at low temperatures. The invention also includes the observation that the products are resistant to hydrolysis and oxidation.

Guerbet carbonates are diesters of carbonic acid. Products having particularly advantageous performance properties are present when $R^1$ and $R^2$ in general formula (I) represent branched alkyl radicals containing 16 to 20 carbon atoms.

The present invention also relates to a process for the production of Guerbet carbonates, characterized in that
a) Guerbet alcohols corresponding to formula (II)

in which $R^1$ is a branched alkyl radical containing 12 to 44 carbon atoms,
are transesterified at elevated temperature with dialkyl carbonates corresponding to formula (III)

in which $R^3$ is a linear alkyl radical containing 1 to 12 carbon atoms,
in the presence of alkali metal or alkaline earth metal compounds and
b) the transesterification products are treated with a filter aid and subsequently filtered.

Branched fatty alcohols of the Guerbet alcohol type are known substances which may be obtained by the relevant methods of preparative organic chemistry. A conventional process for their production comprises condensing ("guerbetizing") primary linear alcohols in the presence of basic catalysts which proceeds via the intermediate stages of the aldehydes and aldols (Soap Cosm. Chem. Spec., 52 (1987)).

Guerbet alcohols suitable as starting materials for the production of the Guerbet carbonates may contain 12 to 44 carbon atoms. Guerbet alcohols corresponding to general formula (II), in which $R^1$ is a branched alkyl radical containing 16 to 20 carbon atoms, are particularly suitable. Accordingly, preferred Guerbet alcohols are those obtained by guerbetization of fatty alcohols containing 8 to 10 carbon atoms. Mixtures of various Guerbet alcohols may also be used for the transesterification reaction.

Dialkyl carbonates are also known substances which may be obtained by the relevant methods of preparative organic chemistry. One process for their production comprises, for example, reacting primary alcohols with phosgene or chloroformic acid ester (J. Chem. Soc., 117, 708 (1920), J. Prakt. Chem. 22, 353 (1980)).

Dialkyl carbonates suitable as starting materials for the production of the Guerbet carbonates aye, for example, dipropyl carbonate, dibutyl carbonate, dioctyl carbonate or di lauryl carbonate. However, dialkyl carbonates corresponding to formula (III), in which $R^3$ is a methyl or ethyl radical, are preferably used. Accordingly, the preferred dialkyl carbonates are dimethyl and diethyl carbonate.

The synthesis of the products according to the invention may be carried out in known manner by transesterification of the dialkyl carbonates with the Guerbet alcohols in the presence of basic catalysts (Houben-Weyl, Methoden der Organischen Chemie, 4th Edition, Vol. E4, pages 66 et seq.).

Suitable alkaline catalysts are alkali metal or alkaline earth metal compounds, more particularly alkali metal or alkaline earth metal hydroxides, alcoholates, carbonates or hydrogen carbonates. A solution of sodium methylate in methanol is preferably used.

The alkali metal or alkaline earth metal compounds may be used for the transesterification reaction in quantities of 1 to 10% by weight and preferably in quantities of 1 to 5% by weight, based on the Guerbet alcohols.

The Guerbet alcohols and the dialkyl carbonates may be used in molar ratios of 1:10 to 10:1. To produce symmetrical Guerbet carbonates, i.e. products obtained by transesterification of both ester groups of the dialkyl carbonate, it has proved to be of advantage to use the alcohol component in a molar excess. A molar ratio of 1:1 to 5:1 and, more particularly, 1:1 to 2:1 has been found to be optimal.

To produce asymmetrical carbonates, i.e. products obtained by transesterification of only one of the two ester groups of the dialkyl carbonate, the dialkyl carbonate is advantageously used in a molar excess. A molar ratio of Guerbet alcohol to dialkyl carbonate of 1:2 to 1:5 has been found to be optimal.

The transesterification of the dialkyl carbonates may be carried out at temperatures of 80° to 290° C. It has proved to be of advantage to carry out the reaction at temperatures of 80° to 150° C. in order to reduce the exposure of the products to high temperatures.

The alcohol released during the transesterification is continuously distilled off and, accordingly, is removed from the reaction equilibrium. Where dimethyl carbonate is used as the starting material, an azeotrope containing methanol and the dialkyl carbonate is formed during the reaction and can be removed particularly easily. Traces of unreacted starting materials or of the alcohol released may subsequently be removed by treating the crude product in vacuo at temperatures below 150° C.

On completion of the transesterification reaction, the product which is still basic has to be neutralized. This is advantageously done by treatment with neutral or acidic filtration aids, for example aluminas or layer silicates of the Tonsil ® or Celite ® type. The filtration aids are added to the reaction mixture in quantities of 0.1 to 10% by weight and preferably in quantities of 0.5 to 2% by weight, based on the Guerbet carbonates. After separation of the additives, for example by filtration or centrifugation, the Guerbet carbonates are obtained in the form of substantially neutral or mildly basic, clear light-colored liquids.

The Guerbet carbonates according to the invention are of low viscosity, have good lubricating properties and are present as clear liquids, even at temperatures of −25° C. They are suitable as lubricants and for the production of lubricants.

The following Examples are intended to illustrate the invention without limiting it in any way.

EXAMPLES

EXAMPLE 1

Bis-$C_{16}$-Guerbet Carbonate 1666 g (6 mol) of a $C_{16}$ Guerbet alcohol (Gerbitol ® G16, hydroxyl value 202, saponification value 6.2, a product of Henkel KGaA) were introduced into a 2 liter three-necked flask equipped with a stirrer, internal thermometer and distillation column and 446 g (4.95 mol) dimethyl carbonate and 38 g of a 30% by weight solution of sodium methylate in methanol were subsequently added. The mixture was then heated under nitrogen for 1 h to 80° C. The reaction temperature was then increased to 95° C. and raised over a period of 5 h to 150° C., an azeotrope containing excess dimethyl carbonate and methanol distilling off. The crude Guerbet carbonate formed was then freed from residual methanol in a water jet vacuum at temperatures below 150° C. Finally, the product was stirred with 30 g, corresponding to 1.5% by weight, Tonsil ®—based on the Guerbet carbonate formed—and purified by filtration. The bis-$C_{16}$-Guerbet carbonate was obtained in the form of a clear liquid. The yield amounted to 97% of the theoretical.

Characteristic data of the product:
Hydroxyl value: 10.8
Pour point: $< -50°$ C.
Cloud point: $< -50°$ C.
Viscosity: 37 mPas

EXAMPLE 2

Bis-$C_{20}$-Guerbet carbonate 1690 g (5 mol) $C_{20}$ Guerbet alcohol (Guerbitol ® G20, hydroxyl value 166, saponification value 5, a product of Henkel KGaA) were reacted as in Example 1 with 371 g (4.12 mol) dimethyl carbonate and 32 g of a 30% by weight solution of sodium methylate in methanol. The bis-$C_{20}$-Guerbet carbonate was obtained in the form of a clear liquid. The yield amounted to 96% of the theoretical.

Characteristic data of the product
Hydroxyl value: 5.7
Pour point: $-25°$ C.
Cloud point: $-28°$ C.
Viscosity: 62 mPas The pour point and cloud point were determined in accordance with DIN 51 601 and DIN ISO 3015. The viscosities were measured in a Höppler viscosimeter.

We claim:

1. A Guerbet carbonate of the formula

$$R^1-O-\overset{\overset{\displaystyle O}{\|}}{C}-O-R^2 \qquad (I)$$

in which $R^1$ and $R^2$ are branched alkyl radicals from Guerbet alcohols containing from 16 to 20 carbon atoms.

2. The Guerbet carbonate of claim 1 which is bis-$C_{20}$-Guerbet carbonate.

3. A lubricant composition comprising a lubricating quantity of a Guerbet carbonate of claim 2.

4. The Guerbet carbonate of claim 1 which is bis-$C_{16}$-Guerbet carbonate.

5. A lubricant composition comprising a lubricating quantity of a Guerbet carbonate of claim 4.

6. A lubricant composition comprising a lubricating quantity of a Guerbet carbonate of claim 1.

* * * * *